United States Patent
Roy

(10) Patent No.: US 12,295,752 B2
(45) Date of Patent: May 13, 2025

(54) PERITONEAL DIALYSIS SYSTEM

(71) Applicant: MOZARC MEDICAL US LLC, Minneapolis, MN (US)

(72) Inventor: Arindam Roy, Bangalore (IN)

(73) Assignee: Mozarc Medical US LLC, Minneapolis, MN (US)

( * ) Notice: Subject to any disclaimer, the term of this patent is extended or adjusted under 35 U.S.C. 154(b) by 0 days.

(21) Appl. No.: 17/371,849

(22) Filed: Jul. 9, 2021

(65) Prior Publication Data
US 2023/0008094 A1   Jan. 12, 2023

(51) Int. Cl.
*A61B 5/145* (2006.01)
*A61B 5/00* (2006.01)
*A61M 1/28* (2006.01)

(52) U.S. Cl.
CPC ........ *A61B 5/6866* (2013.01); *A61B 5/14503* (2013.01); *A61B 5/14532* (2013.01); *A61B 5/4839* (2013.01); *A61M 1/282* (2014.02); *A61M 1/287* (2013.01)

(58) Field of Classification Search
CPC .............. A61B 5/6866; A61B 5/14503; A61B 5/14532; A61B 5/4839; A61M 1/282; A61M 1/287; A61M 1/28; A61M 1/159
See application file for complete search history.

(56) References Cited

U.S. PATENT DOCUMENTS

| | | | | |
|---|---|---|---|---|
| 2010/0298751 | A1* | 11/2010 | Schulte | A61M 1/342 604/4.01 |
| 2013/0303865 | A1* | 11/2013 | Rebec | A61B 5/0013 600/309 |
| 2017/0367646 | A1* | 12/2017 | Schmidt | A61B 5/4812 |
| 2018/0353670 | A1* | 12/2018 | Kommala | G16H 20/60 |
| 2020/0030517 | A1* | 1/2020 | Basati | A61B 5/14507 |
| 2020/0155748 | A1* | 5/2020 | Gerber | A61B 5/14503 |
| 2020/0179583 | A1* | 6/2020 | Hobot | A61B 5/4836 |
| 2021/0338913 | A1* | 11/2021 | Elahi | G16H 10/60 |
| 2022/0370695 | A1* | 11/2022 | Wabel | A61M 1/14 |

OTHER PUBLICATIONS

Shapiro, "Diabetes and Peritoneal Dialysis", Retrieved from: https://www.davita.com/treatment-services/peritoneal-dialysis/diabetes-and-peritoneal-dialysis, Retrieved on May 21, 2021, 2 pp.
U.S. Appl. No. 17/397,358, filed Aug. 9, 2021, naming inventor Manda.

* cited by examiner

*Primary Examiner* — Jay B Shah
*Assistant Examiner* — Grace L Rozanski

(57) ABSTRACT

In some examples, a system includes a glucose sensor configured to generate a signal indicative of a blood glucose level of a patient, a medical device configured to deliver insulin to the patient, a peritoneal dialysis (PD) device, and control circuitry. The control circuitry is configured to control the PD device to deliver PD therapy to a patient during a PD cycle, determine a blood glucose level of the patient during the PD cycle based on a signal from the glucose sensor, determine that the blood glucose level is greater than or equal to a predetermined blood glucose level threshold, and control the medical device to deliver insulin to the patient in response to determining the blood glucose level is greater than or equal to the predetermined blood glucose level threshold.

19 Claims, 4 Drawing Sheets

PERITONEAL DIALYSIS SYSTEM

TECHNICAL FIELD

The present disclosure relates to peritoneal dialysis.

BACKGROUND

Peritoneal dialysis (PD) may be used to remove waste products from blood of a patient when the kidneys of the patient are no longer able to adequately do so. During PD, a PD cycler delivers a dialysate through a catheter into a peritoneal cavity of a patient. The peritoneum of the patient acts as a membrane through which waste products are removed from the blood of the patient via osmosis and diffusion. Waste products and fluid pass from the blood of the patient, through the peritoneum, and into the dialysate. After a dwell period, the PD cycler removes an effluent fluid from the peritoneal cavity, which includes the dialysate and filtered waste products, from the patient's peritoneal cavity through the catheter.

SUMMARY

This disclosure describes example devices, systems, and techniques for monitoring and controlling a PD system and one or more related patient parameters. In examples described herein, a PD system configured to provide PD therapy to a patient is also configured to control an insulin delivery device (also referred to herein as a pump) based on a blood glucose level of a patient, which may improve the efficacy of the PD therapy. In examples in herein, a PD device is configured to deliver dialysate to and extract an effluent fluid from a peritoneal cavity of a patient, a glucose sensor is configured to generate a signal indicative of a blood glucose level of the patient, an insulin pump is configured to deliver insulin to the patient, and a computing device including control circuitry is configured to receive the signal from the glucose sensor and control the insulin pump and PD therapy parameters based on the received signal.

In some examples, control circuitry is configured to operate the blood glucose sensor and the insulin pump in a closed loop manner to control the blood glucose level of the patient to be within a predetermined range during a PD cycle and/or during portions of a PD cycle such as during a dialysate dwell time of a PD cycle. For example, the control circuitry may be configured to receive a signal from the blood glucose sensor, the signal being indicative of the blood glucose level of the patient, at one or more times during one or more PD cycles. The control circuitry may be further configured to cause the insulin pump to deliver insulin to the patient based on the received signal. For example, the control circuitry may determine that a blood glucose level of the patient is greater than or equal to a predetermined blood glucose level threshold and, in response to making such a determination, cause the insulin pump to deliver insulin to the patient to help reduce the blood glucose level to be lower than the blood glucose level threshold. Reducing the blood glucose level of the patient during a PD cycle may improve the effectiveness of the PD, e.g., via improving ultrafiltration by maintaining or increasing a glucose concentration difference between the PD dialysate and the patient's blood.

In some examples, the control circuitry may be further configured to cease a PD cycle, or recommend to a user (e.g., the patient, a clinician, a patient caretaker, or the like) to cease a PD cycle until the blood glucose level of the patient reduces to below the blood glucose level threshold. In other words, the control circuitry may cause the insulin pump to deliver insulin based on the determined blood glucose level of the patient in order to bring the blood glucose level of the patient within a predetermined range, e.g., less than the blood glucose level threshold, cause the PD cycle to cease (or recommend a user cease the PD cycle), wait until the blood glucose level is within the predetermined range, and then cause the PD therapy to resume (or recommend that the user resume the therapy).

In some examples, the control circuitry may be further configured to determine one or more PD therapy parameters based on patient characteristics and blood glucose level determinations. The one or more PD therapy parameters can include, for example, one dialysate glucose concentration, alternative PD dialysate solutes other than glucose such as a glucose polymer and/or an amino acid, a PD dialysate volume and dwell time, an ultrafiltration volume, and/or a number of PD cycles and/or rate within a time period, e.g., per day and/or overnight. The patient characteristics can include, for example, transport characteristics of the patient (e.g., an ultrafiltration rate of the patient's peritoneum), sensed blood glucose level of the patient, and/or the dialysis needs of the patient (e.g., a PD dialysis ultrafiltration goal such as a particular amount of fluid, waste, and/or toxins (such as urea and creatinine) to be removed).

Clause 1: A method includes controlling, by control circuitry, a peritoneal dialysis (PD) device to deliver PD therapy to a patient during a PD cycle; determining, by the control circuitry, a blood glucose level of the patient during the PD cycle; determining, by the control circuitry, the blood glucose level is greater than or equal to a predetermined blood glucose level threshold; and controlling, by the control circuitry and in response to determining the blood glucose level being greater than or equal to the predetermined blood glucose level threshold, a medical device to deliver insulin to the patient.

Clause 2: The method of clause 1, wherein determining the blood glucose level comprises receiving, by the control circuitry, a signal indicative of the blood glucose level from a glucose sensor.

Clause 3: The method of clause 2, further includes sensing, by the glucose sensor, the blood glucose level of the patient subcutaneously.

Clause 4: The method of any one of clauses 1 through 3, further includes controlling, by the control circuitry, the PD device to cease delivering the PD therapy to the patient in response to determining that the blood glucose level is greater than or equal to the predetermined blood glucose level threshold.

Clause 5: The method of clause 3 or clause 4, wherein the blood glucose level of the patient comprises a first blood glucose level at a first time, the method further includes determining, by the control circuitry, a second blood glucose level of the patient at a second time; and controlling the PD device to resume delivery of the PD therapy to the patient in response to determining that the second blood glucose level is less than the predetermined blood glucose level threshold.

Clause 6: The method of any one of clauses 1 through 5, further includes determining, by the control circuitry and based on the blood glucose level of the patient and a PD dialysis ultrafiltration goal, a PD dialysate glucose concentration; determining, by the control circuitry and based on a transport characteristic of the patient, the PD dialysate glucose concentration, the blood glucose level of the patient, and the PD dialysis ultrafiltration goal, an ultrafiltration volume for the patient and a PD dialysate dwell time; and controlling, by the control circuitry, the PD device to deliver the PD therapy to the patient in accordance with the ultrafiltration volume, the PD dialysate glucose concentration, and the PD dialysate dwell time.

Clause 7: The method of clause 6, wherein the blood glucose level of the patient comprises a first blood glucose level at a first time, wherein the PD dialysate glucose concentration is a first PD dialysate glucose concentration, wherein the ultrafiltration volume is a first ultrafiltration volume, wherein the PD dialysate dwell time is a first PD dialysate dwell time, the method further includes determining, by the control circuitry, a second blood glucose level of the patient at a second time after delivery of PD to the patient; determining, by the control circuitry and based on the second blood glucose level of the patient, a second PD dialysate glucose concentration; determining, based on the transport characteristic of the patient and the second PD dialysate glucose concentration and the second blood glucose level of the patient, a second ultrafiltration volume for the patient and a second PD dialysate dwell time; and controlling, by the control circuitry, the PD device to deliver the PD therapy to the patient in accordance with the second ultrafiltration volume, the second PD dialysate glucose concentration, and the second PD dialysate dwell time.

Clause 8: The method of any one of clauses 1 through 7, further includes determining, by the control circuitry and based on the blood glucose level of the patient, a PD dialysate comprising an alternate osmotic solute and a PD dialysate concentration of the alternate osmotic solute; determining, by the control circuitry and based on a transport characteristic of the patient and the PD dialysate alternate osmotic solute concentration and the blood glucose level of the patient, an ultrafiltration volume and a PD dialysate dwell time; and controlling, by the control circuitry, the PD device to deliver the PD therapy to the patient in accordance with the ultrafiltration volume, the PD dialysate alternate osmotic solute concentration, and the PD dialysate dwell time.

Clause 9: The method of clause 8, wherein the alternate osmotic solute comprises at least one of a glucose polymer or an amino acid.

Clause 10: The method of any one of clauses 1 through 9, further comprising delivering, by the medical device, insulin to the patient subcutaneously.

Clause 11: The method of any one of clauses 1 through 10, wherein determining the blood glucose level of the patient comprises determining the blood glucose level of the patient at first predetermined intervals during delivery of PD therapy to the patient, wherein controlling the medical device to deliver insulin to the patient comprises controlling the medical device to deliver insulin to the patient at second predetermined intervals and while the most recent determined blood glucose level is greater than or equal to the blood glucose level threshold.

Clause 12: A system includes a glucose sensor configured to generate a signal indicative of a blood glucose level of a patient; a medical device configured to deliver insulin to the patient; a peritoneal dialysis (PD) device; and control circuitry configured to: control the PD device to deliver PD therapy to a patient during a PD cycle, determine, based on the signal, a blood glucose level of the patient during the PD cycle, determine that the blood glucose level is greater than or equal to a predetermined blood glucose level threshold, and control, in response to determining the blood glucose level is greater than or equal to the predetermined blood glucose level threshold, the medical device to deliver insulin to the patient.

Clause 13: The system of clause 12, wherein the glucose sensor is configured to sense the blood glucose level of the patient subcutaneously, wherein the medical device is configured to deliver insulin to the patient subcutaneously.

Clause 14: The system of any of clause 12 or clause 13, wherein the blood glucose level is a first blood glucose level determined at a first time, wherein the control circuitry is further configured to: control the PD device to cease delivering the PD therapy to the patient in response to determining that the first blood glucose level is greater than the predetermined blood glucose level threshold; determine a second blood glucose level of the patient at a second time; and control the PD device to resume delivery of the PD therapy to the patient in response to determining that the second blood glucose level is less than the predetermined blood glucose level threshold.

Clause 15: The system of any of clauses 12 through 14, wherein the control circuitry is further configured to: determine, based on the blood glucose level of the patient and a PD dialysis ultrafiltration goal, a PD dialysate glucose concentration; determine, based on a transport characteristic of the patient, the PD dialysate glucose concentration, the blood glucose level of the patient, and the PD dialysis ultrafiltration goal, an ultrafiltration volume for the patient and a PD dialysate dwell time; and control the PD device to deliver the PD therapy to the patient in accordance with the ultrafiltration volume, the PD dialysate glucose concentration, and the PD dialysate dwell time.

Clause 16: The system of clause 15, wherein the blood glucose level of the patient comprises a first blood glucose level at a first time, wherein the PD dialysate glucose concentration is a first PD dialysate glucose concentration, wherein the ultrafiltration volume is a first ultrafiltration volume, wherein the PD dialysate dwell time is a first PD dialysate dwell time, wherein the control circuitry is further configured to: determine a second blood glucose level of the patient at a second time after delivery of PD to the patient; determine based on the second blood glucose level of the patient, a second PD dialysate glucose concentration; determine, based on the transport characteristic of the patient and the second PD dialysate glucose concentration and the second blood glucose level of the patient, a second ultrafiltration volume for the patient and a second PD dialysate dwell time; and control the PD device to deliver the PD therapy to the patient in accordance with the second ultrafiltration volume, the second PD dialysate glucose concentration, and the second PD dialysate dwell time.

Clause 17: The system of any one of clauses 12 through 16, wherein the control circuitry is further configured to: determine, based on the blood glucose level of the patient, a PD dialysate comprising an alternate osmotic solute and a PD dialysate alternate osmotic solute concentration of the alternate osmotic solute; determine, based on a transport characteristic of the patient and the PD dialysate alternate osmotic solute concentration and the blood glucose level of the patient, an ultrafiltration volume and a PD dialysate dwell time; and control the PD device to deliver the PD therapy to the patient in accordance with the ultrafiltration volume, the PD dialysate alternate osmotic solute concentration, and the PD dialysate dwell time.

Clause 18: The system of clause 17, wherein the alternate osmotic solute comprises at least one of a glucose polymer or an amino acid.

Clause 19: The system of any one of clauses 12 through 18, wherein the control circuitry is further configured to: determine the blood glucose level of the patient at predetermined intervals during delivery of PD to the patient; and control the medical device to deliver insulin to the patient at predetermined intervals while the most recent determined blood glucose level is greater than or equal to the blood glucose level threshold.

Clause 20: A system includes a peritoneal dialysis (PD) cycler; and control circuitry configured: determine a first blood glucose level of a patient at a first time, determine that the first blood glucose level is greater than or equal to a predetermined blood glucose level threshold of the patient; control the PD cycler to cease delivering PD therapy to the patient in response to determining that the first blood glucose level is greater than or equal to the predetermined blood glucose level threshold, determine a second blood glucose level of the patient at a second time after the first time, determine that the second blood glucose level is less than the predetermined blood glucose level threshold of the patient, and control the PD cycler to resume delivery of the PD therapy to the patient in response to determining that the second blood glucose level is less than the predetermined blood glucose level threshold.

Clause 21: The system of clause 20, further comprising a glucose sensor configured to generate a signal indicative of the first and second blood glucose levels of the patient, wherein the control circuitry is configured to receive the signal from the glucose sensor and determine the first and second blood glucose levels of the patient based on the signal.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
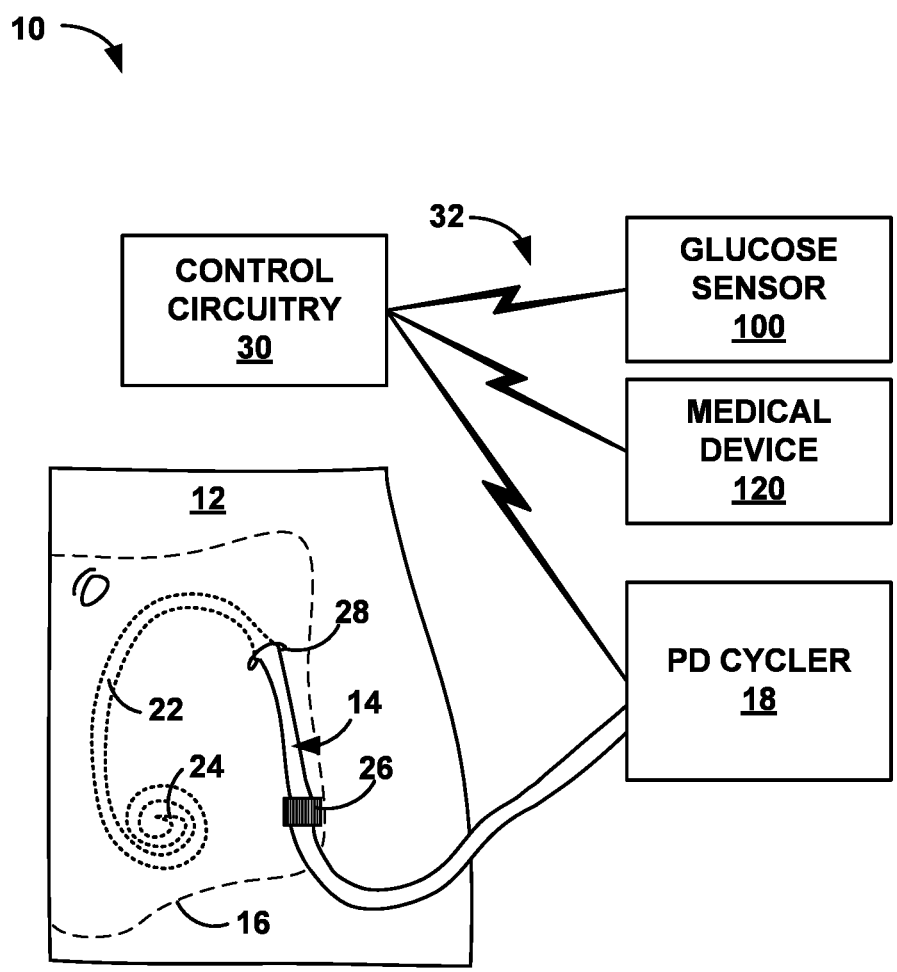
FIG. 1 is a diagram illustrating an example PD system configured to provide a patient with PD treatment.

PD systems, as well as devices, systems, and techniques for monitoring and controlling a peritoneal dialysis (PD) system and one or more related patient parameters are described herein. In examples described herein, a PD system includes a PD device such as a PD cycler, or manual PD dialysate filling and draining, and is configured to deliver dialysate and extract an effluent fluid from a peritoneal cavity of a patient via at least one catheter. The PD system also includes a glucose sensor configured to generate a signal indicative of a blood glucose level of the patient, a medical device (also referred to herein as an insulin pump or an insulin delivery device) configured to deliver insulin to the patient, and a computing device including control circuitry configured to control the PD system and the medical device to control the glucose levels of the patient during PD.

Slow sustained ultrafiltration conferred by PD can be effective for diabetic uremic patients. Diabetic patients with end-stage renal disease (ESRD) may have multiple cardiovascular and metabolic complications. The rapid and intermittent extracorporeal removal of solutes and water via hemodialysis can result in dialysis-induced hypotension, coronary ischemia, and/or arrhythmia, which can possibly lead to worsening cardiovascular status in the diabetic patients. Additional advantages of PD versus hemodialysis for diabetic patients with ESRD include one or more of improved preservation of residual renal function, elimination of the risk of thrombosis or stenosis at an arteriovenous access site, vascular capital preservation (e.g., PD can eliminate a need to access a blood vessel of the patient for dialysis therapy, thereby preserving the vasculature), avoidance of peripheral and coronary steal syndromes, better blood pressure control, no need of systemic anticoagulation, fewer episodes of progressive retinopathy, or feasibility of elective intraperitoneal insulin dosage.

There can be challenges associated with PD for some patients, such as diabetic patients. Uremic patients treated with PD may have a higher risk of deregulated metabolic response because of increased glucose absorption from the dialysate, and hyperglycemia prevalence may be greater in PD patients than hemodialysis patients. One of the implications associated with hyperglycemia is the activation of the thirst mechanism, leading to difficulty in managing fluid balance. For example, the more the glucose absorption from the dialysate increases, the higher the glucose concentration in the PD dialysate needs to be (e.g., from 1.5% PD fluid to 2.5% PD fluid), which creates more thirst and fluid intake by the patient. In addition, PD patients with diabetes may have increased extracellular volume, which may be a precursor to fluid overload.

Glucose helps remove waste products from the blood through the peritoneal membrane. A difference in the glucose concentration between the dialysate and the patient's blood is necessary for filtration through the peritoneum, and therefore the higher the glucose absorption by the patient, the higher the glucose concentration is needed in the dialysate. Glucose attracts the water out of the blood, and with some non-diabetic PD patients, the use of hypertonic PD bags may be increased in response to fluid overload. However, the increased use of hypertonic PD bags can increase the amount of glucose absorbed by patient, which may create more thirst in a diabetic patient and consequently an increase of fluid intake by the patient, which may ultimately negatively impacting glycemic control and peritoneal integrity.

There may be a risk of hypertonicity in diabetes patient with severe clinical manifestations due to the use of hypertonic PD dialysates. Hypertonic dextrose dialysate may also inhibit the proliferation of mesothelial cells and cause increased mesothelial production of transforming growth factor, potentially leading to peritoneal fibrosis.

In examples described herein, a PD system is configured to deliver PD therapy with glycemic control, which may help reduce absorption of glucose by a patient during PD therapy while still meeting an ultrafiltration goal. For example, because a relatively large difference in glucose concentration between the patient's blood and the PD dialysate is required for effective PD, glycemic control (e.g., via a reduction of the glucose concentration in the patient's blood) may enable the use of a relatively low glucose concentration dialysate. Glycemic control during PD may provide a more effective PD therapy (e.g., for a given PD cycle) by other mechanisms as well. For example, glycemic control may enable the use of higher concentration dialysate, which may provide an increased ultrafiltration rate, while reducing thirst in a diabetic patient and reducing the fluid intake by the patient and the resulting fluid overload.

According to some examples disclosed herein, systems and methods of PD therapy with glycemic control may include controlling a medical device to deliver doses of insulin to a patient via a closed loop control technique. The closed loop glycemic control system includes an insulin pump and a blood glucose sensor such as a continuous glucose monitor (CGM) attached to the patient, and a PD device. In some examples, the patient may activate the closed loop glycemic control system manually during a PD treatment. In other examples, a computing device may be in communication with the insulin pump, CGM, and PD device via a wireless or a wired communication connection and may automatically activate and control the closed loop glycemic control system. For example, control circuitry of the computing device may be configured to execute an algorithm to coordinate glycemic control with PD cycling and PD therapy parameters. The control circuitry may set a blood glucose concentration threshold and/or setpoint as needed based on the PD therapy and glycemic control.

The closed loop glycemic control system (including the control circuitry) may be configured to operate and deliver insulin to a patient before, during, or after a PD cycle. A PD cycle may include delivery of a PD dialysate to a peritoneal cavity of the patient, e.g., via a PD cycler, a dwell time in which the PD dialysate draws fluid and waste material through the peritoneum of the patient via osmosis, and removal of the fluid from the peritoneal cavity of the patient, e.g., via the PD cycler. PD therapy and/or treatment may comprise delivering one or more PD cycles to the patient, e.g., periodically, according to a schedule, or in response to a determination that a PD cycle should be delivered to the patient.

In some examples, control circuitry may determine a PD dialysate glucose concentration (e.g., 1.25% dextrose, 2.5% dextrose, 4.25% dextrose, and the like) based on a balance between the ultrafiltration needs of the patient (e.g., a PD dialysis ultrafiltration goal for a given PD cycle or a series of PD cycles) and a determined blood glucose level of the patient, e.g., determined relatively close in time to or at the same time as the PD cycle so as to represent the patient condition at the time of the PD cycle. In some cases, the use of shorter, frequent dialysis exchanges may increase the net ultrafiltration volume relative to the amount of glucose absorbed by the patient. As such, the control circuitry may further determine a PD dialysate volume and dwell time and number of PD cycles based on one or all of the PD dialysis ultrafiltration goal, a determined blood glucose level of the patient, a determined PD dialysate glucose concentration, and a transport characteristic of the patient, e.g., an ultrafiltration rate of the peritoneum of the patient. The control circuitry may then cause, or recommend, delivery of PD to the patient in accordance with the determined PD therapy parameters.

The control circuitry may further be configured to determine the blood glucose level of the patient at certain time intervals during and between PD therapy cycles, and to control delivery of insulin to the patient via an insulin pump based on the determined blood glucose levels of the patient. In some examples, the control circuitry may cause the insulin pump to deliver a bolus or dose of insulin to the patient in response to determining the blood glucose level of the patient is greater than or equal to a predetermined blood glucose level threshold, and in some examples the control circuitry may cause the insulin pump to deliver a bolus or dose of insulin to the patient based on a plurality of determined blood glucose levels, e.g., a trend of increasing blood glucose level measurements, a rate of increase of blood glucose level, and further based on known and/or determined rate of glucose absorption by the patient. For example, the control circuitry may be configured to determine a rate of glucose absorption by the patient based on the PD dialysate volume, dwell time, and glucose concentration as well as measured blood glucose levels, and may be configured to deliver insulin and/or control (or output recommendations regarding) PD therapy delivery based on the measured blood glucose levels, blood glucose levels rate of change, and determined rate of glucose absorption by the patient.

FIG. 1 is a diagram illustrating an example PD system 10 configured to provide patient 12 with PD treatment and glycemic control. PD system 10 includes a catheter 14, which is illustrated as extending into a peritoneal cavity 16 of patient 12, a PD cycler 18, a glucose sensor 100, an medical device 120 (e.g., illustrated as an insulin pump), and control circuitry 30. In some cases, however, PD system 10 may be applied to other mammalian or non-mammalian, non-human patients.

PD cycler 18 is configured to deliver a dialysate into peritoneal cavity 16 via catheter 14. The dialysate remains in peritoneal cavity 16 for a dwell period, which has a duration that is intended to, but may not always be, sufficient for the exchange of waste products across a peritoneum of patient 12 to take place. In some such examples, PD cycler 18 may be disconnected from catheter 14 during the dwell period. In other examples, however, PD cycler 18 remains connected to catheter 14 during the dwell period. After the dwell period, PD cycler 18 removes fluid from peritoneal cavity 16. The fluid drained from peritoneal cavity 16 can be referred to as an effluent fluid, which contains the dialysate and the waste products removed from the blood of patient 12. In some examples, PD cycler 18 may be active cycler configured to move fluid via a pump. In other examples, PD cycler may be a passive cycler configured to move fluid via gravity.

In some examples, the waste products may be removed by the dialysate due to a concentration gradient, e.g., due to the concentration of an osmotic agent in the dialysate, created in peritoneal cavity 16 when peritoneal cavity 16 is filled with the dialysate, which drives ultrafiltration and convective solute removal. The dialysate may include water, and dextrose or other sugars, salt, electrolytes, ions, amino acids, glucose polymers, and/or minerals as the osmotic agent. In some examples, the dialysate is dextrose-based, e.g., includes dextrose as the osmotic agent. Examples of dextrose-based dialysates include, but are not limited to, Dianeal available from Baxter Healthcare Corporation of Deerfield, IL and Delflex® available from Fresenius Medical Care of Waltham, MA In other examples, the dialysate may be characterized in having relatively low amounts of glucose degradation products (GDPs) and/or having a neutral pH (e.g., a pH of or close to 7). Examples of such dialysates include, but are not limited to, Physioneal available from Baxter Healthcare Corporation of Deer Field, IL, balance available from Fresenius Medical Care of Waltham, MA, and bicaVera® available from Fresenius Medical Care of Waltham, MA In yet other examples, dialysates may be icodextrin-based, such as Extraneal available from Baxter Healthcare Corporation of Deer Field, IL, or amino acid-based, such as Nutrineal™ available from Baxter Healthcare Corporation of Deer Field, IL.

In order to deliver the dialysate into peritoneal cavity 16 and remove the effluent fluid from peritoneal cavity 16, PD cycler 18 is connected to catheter 14, such as via an adapter 26, which provides the necessary mechanical connection between catheter 14 and PD cycler 18 to establish fluid communication therebetween. Catheter 14 may be any fluid delivery conduit capable of being inserted into peritoneal cavity 16 and connected to PD cycler 18 to facilitate PD treatment of patient 12. Catheter 14 defines an inner lumen 22 through which fluid may flow from PD cycler 18 to peritoneal cavity 16 and from peritoneal cavity 16 to PD cycler 18. Inner lumen 22 terminates at a distal opening, which can be at a distal-most end 24 of catheter 14, as shown in FIG. 1, and/or along a sidewall proximal to the distal-most end of catheter 14. Catheter 14 may be inserted into patient 12 via an exit site 28, and be configured to remain in patient 12 on a long-term basis, with a portion of catheter 14 remaining within peritoneal cavity 16 and a portion of catheter 14 residing outside of patient 12.

Catheter 14 can have any suitable configuration. For example, the portion of catheter 14 that remains within peritoneal cavity 16 may be straight or curvilinear, such as coiled (e.g., pig-tailed) as shown in FIG. 1. In some examples, a distal portion of catheter 14 has a swan neck (e.g., a curved portion 40, shown in FIGS. 2 and 3, curved up to about 180 degrees), which may help position catheter 14 at exit site 28 as intended. Catheter 14 has any suitable length for accommodating PD treatment. For example, catheter 14 may be between about 57 cm and about 62 cm in length (e.g., from adapter 26 to a distal-most end of catheter 14 within peritoneal cavity 16), and may be between about 2.5 mm and about 3.5 mm in diameter. In other examples, other shapes, sizes (e.g., length or diameter), and/or configurations may be used. An example of catheter 14 includes, but is not limited to, the Argyle™ Peritoneal Dialysis Catheter available from Medtronic, Inc. of Minneapolis, MN.

Glucose sensor 100 is configured to sense a blood glucose level of patient 12 and generate a signal that is indicative of the blood glucose level of patient 12. For example, glucose sensor 100 may be a CGM configured to determine a blood glucose level and/or concentration of patient 12 subcutaneously at certain time intervals, e.g., every several minutes. In some examples, glucose sensor 100 may determine the blood subcutaneously via an enzymatic reaction with glucose molecules in interstitial tissue and generating a measurable electric current. In other example, glucose sensor 100 may be any other type of glucose sensor and/or measuring device configured to sense a blood glucose level of patient 12 and generate a signal that is indicative of the blood glucose level of patient 12, e.g., a system comprising test strips and an electronic blood glucose meter.

In some examples, glucose sensor 100 may be configured to communicate a blood glucose level directly to control circuitry 30. For example, glucose sensor 100 may generate and send the signal that is indicative of the blood glucose level of patient 12 to control circuitry 30, or provide control circuitry 30 with the signal after receiving a query from control circuitry 30 for a blood glucose level. In other examples, patient 12, a clinician, a patient caretaker, or the like may manually input a blood glucose level of patient 12 into a glucose sensor 100 which may generate and communicate the signal to control circuitry 30. For example, patient 12 may do a finger prick test using a test strip and a blood glucose meter, read the blood glucose level from the blood glucose meter and input the result into an application on a computing device, e.g., a computer, a mobile phone, a laptop, a computing device configured to operate PD cycler 18, or any suitable device configured to communicate with control circuitry 30 and send or otherwise provide the signal indicative of the blood glucose level of patient 12 to control circuitry 30. In other words, in some examples, blood glucose sensor 100 may be a manual system including a user, a blood glucose level sensing apparatus and procedure (e.g., finger prick test with test strip read by a blood glucose meter), and a reporting and signal generation apparatus and procedure, e.g., a user inputting value into a device configured to communicate with control circuitry 30.

Medical device 120 is configured to delivery insulin to patient 12. For example, medical device 120 may be an insulin pump configured to deliver insulin to patient 12 subcutaneously. In other example, medical device 120 may be an insulin syringe or an insulin pen operated manually by patient 12, a clinician, a patient caretaker, or the like.

In some examples, medical device 120 is configured to delivery insulin to patient 12 automatically or to be directly controlled by control circuitry 30. For example, medical device 120 may receive a signal from control circuitry 30 and deliver insulin to patient 12 in response to receiving the signal. In other examples, control circuitry 30 may generate a signal and/or output to a user interface directing a clinician, a patient caretaker, or the like to deliver insulin to patient 12, e.g., manually via a syringe or insulin pen. In other words, medical device 120 may be a manual system including a user, an insulin delivery apparatus and procedure (e.g., syringe or insulin pen), and a command apparatus and procedure for directing the delivery of insulin via the insulin delivery apparatus and procedure, e.g., a device configured to communicate instructions such as via a user interface.

PD system 10 includes control circuitry 30, which is configured to receive one or more signals generated by glucose sensor 100, medical device 120, and PD cycler 18 and determine information about PD system 10 and/or patient 12 based on the received signals. The received information can include, for example, a blood glucose level of patient 12, one or more PD parameters of PD cycler 18, and one or more parameters of medical device 120. Control circuitry 30 is configured to use such information about PD system 10 or patient 12 to adjust the PD treatment delivered by PD cycler 18 and/or coordinate PD treatment with glycemic control via insulin delivery by medical device 120 to help improve the efficacy of the PD treatment and/or control the blood glucose level of patient 12 before, during, or after PD treatment.

Control circuitry 30 may be configured to control PD cycler 18 to deliver PD therapy to patient 12 during a PD cycle. For example, control circuitry 30 may cause PD cycler 18 to deliver a dialysate into peritoneal cavity 16 via catheter 14 and may cause PD cycler 18 to remove fluid from peritoneal cavity 16 via catheter 14, e.g., after a dwell time.

Control circuitry 30 is also configured to determine a blood glucose level of patient 12 before, during, or after the PD cycle. For example, control circuitry 30 may receive a signal indicative of the blood glucose level of patient 12 from glucose sensor 100. In some examples, control circuitry 30 may send a query signal to glucose sensor 100 to request a blood glucose level, and blood glucose sensor 100 may send the signal indicative of the blood glucose level of patient 12 in response. In other examples, glucose sensor 100 automatically sends the signal to control circuitry 30 without the need for query signals. In some example, control circuitry 30 may receive multiple signals indicative of the blood glucose level of patient 12 from glucose sensor 100 at different times, e.g., at regular time intervals or at times according to a schedule.

Control circuitry 30 may be configured to control medical device 120 to deliver insulin to patient 12. For example, control circuitry 30 may determine that a blood glucose level of patient 12 is greater than or equal to a predetermined blood glucose level threshold, and may send a command signal to medical device 120 to cause medical device 120 to deliver insulin to patient 12 in response to such a determination. In other examples, where medical device 120 may be manually controlled by patient 12, a clinician, a patient caretaker, or the like, control circuitry 30 may need to intervene to cause medical device 120 to deliver insulin to patient 12, such as by interacting with a user interface to provide input to medical device 120 indicating that insulin should be delivered to patient 12.

In some examples, control circuitry 30 is configured to control PD cycler 18, glucose sensor 100, and medical device 120 to operate in a closed-loop manner. For example, control circuitry 30 may receive a blood glucose level via a signal from glucose sensor 100 indicative of the blood glucose level of patient 12 at a plurality of time intervals, e.g., regular intervals or at a plurality of predetermined time intervals, during delivery of PD to patient 12. Control circuitry 30 may control medical device 120 to deliver insulin to patient 12 at predetermined time intervals while the most recent blood glucose level is greater than or equal to the blood glucose level threshold. In other examples, control circuitry 30 may generate and output instructions to patient 12, a clinician, a patient caretaker, or the like, to cause insulin to be delivered to patient 12 during deliver of PD therapy.

In some examples, control circuitry 30 is configured to both initiate and/or cease delivery of PD therapy to patient 12 based on a blood glucose level of patient 12. For example, control circuitry 30 may be configured to control PD cycler 18 to cease delivering PD therapy to patient 12 in response to determine that the blood glucose level of patient 12 is greater than or equal to a predetermined blood glucose level threshold. For example, control circuitry 30 may be configured to generate and send a command signal to PD cycler 18 to cease delivery of PD therapy by draining PD dialysate from patient 12 during a dwell time, e.g., cuffing the dwell time short so as to remove the PD dialysate and reduce the rate and/or amount of glucose absorption by patient 12 from the PD dialysate. Control circuitry 30 may be configured to control PD cycler 18 to resume delivery of the PD therapy to patient 12. For example, control circuitry 30 may determine that a second glucose level of patient 12 at a second time after ceasing PD therapy delivery is less than the predetermined blood glucose level and generate and send a command signal to PD cycler 18 to resume delivery of PD therapy to patient 12. PD cycler 18 may then provide PD dialysate to patient 12 via catheter 14.

In some examples, control circuitry 30 is configured to determine PD therapy parameters and control PD cycler 18 to deliver PD therapy to patient 12 based on the determined PD therapy parameters. For example, control circuitry 30 may be configured to determine a PD dialysate glucose concentration, e.g., 1.25% dextrose, 2.5% dextrose, 4.25% dextrose, and the like, to be used by PD cycler 18 to deliver PD therapy to patient 12. For example, control circuitry 30 may determine a PD dialysate glucose concentration based on the glucose level of patient 12, e.g., as sensed by glucose sensor 100, and a PD dialysis ultrafiltration goal. An ultrafiltration goal may be determined by a clinician, or may be determined by an external system and provided to control circuitry 30, or an ultrafiltration goal may be determined by control circuitry 30, e.g., based on PD therapy history and patient information. Control circuitry 30 may further determine an ultrafiltration volume and PD dialysate dwell time for a particular PD cycle, e.g., based on a transport characteristic of patient 12 and the determined PD dialysate glucose concentration and blood glucose level of patient 12. For example, the use of shorter, more frequent dialysis exchanges may increase the net ultrafiltration volume relative to the amount of glucose absorbed by the patient. The ratio of net ultrafiltration volume per amount of glucose absorbed by the patient, e.g., per gram of glucose absorbed, is higher with short PD cycles including a short dwell time as compared to a longer PD cycle including a longer dwell time. This increased ration of net ultrafiltration volume per amount of glucose absorbed applies to patients with a "high" transport characteristic, e.g., "high transporters" with a relatively high fluid transfer rate through the peritoneum, and diabetic patients with an average transport characteristic and requiring a high net ultrafiltration volume. In other words, the longer time that PD dialysate dwells within the peritoneal cavity of the patient, the higher the glucose absorption, but the shorter time that the PD dialysate dwells within the peritoneal cavity of the patient, the less the ultrafiltration volume. However, the ultrafiltration and glucose absorption rates may not be constant over time nor equal, and a higher net ultrafiltration volume per amount of glucose absorbed may be changed via changing certain PD therapy parameters, such as the dwell time and the number of cycles within a period of time. In some examples, the ratio of net ultrafiltration volume per amount of glucose absorbed by the patient is higher with the use of shorter dwell times and more frequent PD cycles including the shortened dwell time.

For example, a transport characteristic such as the amount of fluid and/or uremic concentration that transfers from the body of patient 12 to PD dialysate in the peritoneal cavity 16 through the peritoneum of patient 12 may change over time, e.g., over the course of months or years. A transport characteristic of patient 12 may change because of changes in vasculature of the patient, and may be a measure of the permeability of the peritoneum of patient 12. A transport characteristic, e.g., a transfer amount and/or transfer rate of a fluid, uremic concentration, and the like, may be determined based on a peritoneal functional test performed by a clinician. Control circuitry 30 may be configured to cause PD cycler 18 to deliver PD therapy to patient 12 via the determined ultrafiltration volume and PD dialysate dwell time.

In some examples, control circuitry 30 may be configured to control PD cycler 18 to deliver PD therapy to patient 12 that changes over time, e.g., based on a regimen, a schedule, a plan, or in response to patient information and/or historical or current blood glucose levels of patient 12. For example, patient 12 may have a high need for dialysis and may also have a moderate and/or high blood glucose level. Because the blood glucose level of patient 12 is high, a higher glucose concentration PD dialysate may be needed to reach the ultrafiltration goal, and insulin may be delivered to patient 12 in order to control the blood glucose level of patient 12. After a period of time, the blood glucose level of patient 12 may reduce, e.g., via delivery of insulin to patient 12, via ceasing the dwell of the PD dialysate (e.g., after an initial PD therapy with the high glucose concentration PD dialysate), or both. Patient 12 may then have a reduce blood glucose level, a reduced ultrafiltration goal, or both, and a lower glucose concentration PD dialysate may be used for further PD therapy. In other words, PD system 10 or control circuitry 30 may be configured to change PD therapy settings for patient 12 from high glucose concentration PD therapy to lower glucose concentration PD therapy.

For example, control circuitry 30 may be configured to determine a first set of PD therapy parameters at a first time, e.g., a first PD dialysate glucose concentration, a first PD dialysate volume, and a first PD dialysate dwell time, based on a first ultrafiltration goal, a transport characteristic of patient 12, and a first blood glucose level of patient 12 determined at the first time, e.g., via glucose sensor 100. Control circuitry 30 may be further configured to determine a second blood glucose level of patient 12 at a second time, e.g., via glucose sensor 100, and to determine a second set of PD therapy parameters at the second time based on the transport characteristic of patient 12, a second ultrafiltration goal (which may be the same or different from the first ultrafiltration goal), and the second blood glucose level of patient 12. Control circuitry 30 may be configured to cause PD cycler 18 to deliver PD therapy to the patient in accordance with the determined second set of PD therapy parameters, e.g., a second ultrafiltration volume, a second PD dialysate glucose concentration (e.g., which may be a lower concentration than the first PD dialysate glucose concentration), and a second PD dialysate dwell time.

In some examples, PD system 10 or control circuitry 30 may be configured to change PD therapy settings for patient 12 from a low glucose concentration PD therapy to a higher glucose concentration PD therapy. For example, if the blood glucose level of patient 12 is out of range for which a low glucose concentration PD solution will be effective to achieve an ultrafiltration goal, then control circuitry 30 may cause medical device 120 to deliver insulin to patient 12 and cease PD therapy (e.g., by causing PD cycler 18 to remove fluid from patient 12) if a PD cycle is currently being delivered to patient 12, or wait to deliver a PD cycle to patient 12 until the blood glucose level of patient 12 is within range. For example, control circuitry 30 may receive a second signal from glucose sensor 100 at a second time after delivery of insulin to patient 12 by medical device 120 and determine a second blood glucose level of patient 12, which may be lower and within range such that a lower glucose concentration PD dialysate will be effective in achieving the ultrafiltration goal. Alternatively, if the blood glucose level of patient 12 is out of range for which a low glucose concentration PD solution will be effective to achieve an ultrafiltration goal, then control circuitry 30 may cause PD cycler 18 to deliver PD therapy with a higher glucose concentration PD dialysate to achieve the ultrafiltration goal. Control circuitry may also cause medical device 120 to deliver insulin to patient 12 and control PD therapy parameters such as the volume and dwell time of the higher glucose concentration. Control circuitry 30 may then "step down" and/or reduce the glucose concentration of the PD dialysate for subsequent PD cycles, e.g., while determining and controlling PD therapy parameters such as PD dialysate volume and dwell time and the frequency of subsequent PD cycles, as well as the delivery of insulin to patient 12 via medical device 120. Control circuitry 30 may further request and/or receive one or more signals indicative of the blood glucose level of patient 12 from glucose sensor 100 at one or more times before, during, and after delivery of one or more PD cycles including the higher and/or lower glucose concentration PD dialysate.

In some examples, control circuitry 30 may be configured to determine a PD dialysate including an alternate osmotic solute and its concentration, e.g., an osmotic solute other than glucose. For example, control circuitry 30 may determine an alternate PD dialysate osmotic solute based on the glucose level of patient 12, e.g., as sensed by glucose sensor 100, and a PD dialysis ultrafiltration goal. In some examples, alternate osmotic solute comprises at least one of a glucose polymer or an amino acid, or any suitable alternate osmotic solute. Control circuitry 30 may be configured to determine an ultrafiltration volume and a PD dialysate dwell time based on the alternate osmotic solute and its concentration as well as the glucose level of patient 12, a determined transport characteristic of patient 12, and an ultrafiltration goal. Control circuitry 30 may be configured to cause PD cycler 18 to deliver PD therapy to the patient in accordance with the determined alternate osmotic solute and its concentration, determined ultrafiltration volume and determined PD dialysate dwell time.

In some examples, control circuitry 30 may record and/or send one or more blood glucose levels of patient 12, sensed and determined before, during, and/or after delivery of one or more PD cycles to patient 12, to another device, e.g., an external device such as another computer, a server, a mobile computing device and the like. For example, control circuitry 30 may provide blood glucose level information, alone or in combination with other information such as PD therapy parameters, to a telehealth platform. The blood glucose information may provide information to a clinical team, such as trends of one or more parameters and/or sensed quantities such as blood glucose levels. The blood glucose information may be used, e.g., by a clinician, to prescribe an action to be taken by patient 12, e.g., perform exercise along with a duration, time, and type of exercise, eat or refrain from eating certain foods, receive an insulin dose, or any other suitable action.

Control circuitry 30, as well as other processors, processing circuitry, controllers, control circuitry, and the like, described herein, may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 30 may include multiple components, such as any combination of one or more microprocessors, one or more DSPs, one or more ASICs, or one or more FPGAs, as well as other discrete or integrated logic circuitry, and/or analog circuitry. The functions attributed to control circuitry 30, as well as other processors described herein, may be embodied as firmware, hardware, software or any combination thereof.

In some examples, control circuitry 30 can be part of PD cycler 18, while in other examples, control circuitry 30 can be part of a different device, such as a clinician computing device that is located near PD cycler 18 or remotely located (e.g., more than 50 feet away) from PD cycler 18 and connected to PD cycler 18 via a wired or wireless connection. Although not shown in FIG. 1, control circuitry 30 may be part of a device that includes additional components, such as, but not limited to, a memory, a telemetry module that includes circuitry to facilitate communication between control circuitry 30 and another component, such as glucose sensor 100 and/or medical device 120, and a power source. Similarly, although not shown in FIG. 1, in some examples, one or both of glucose sensor 100 and medical device 120 may include its own processor, a memory, a telemetry module, and/or a power source.

Glucose sensor 100 and/or medical device 120 are configured to transmit respective electrical signals indicative of sensed parameters (e.g., blood glucose level) and/or insulin dose or dosing related to PD system 10 or to patient 12, or both, to control circuitry 30. Control circuitry 30 is configured to transmit signals to control glucose sensor 100 and/or medical device 120, such as to request sensed parameter information from glucose sensor 100 or to control delivery of insulin by medical device 120.

PD cycler 18, glucose sensor 100, medical device 120, and control circuitry 30 are configured to communicate with each other using any suitable communication technique and via any suitable wired or wireless communication channels. In the example shown in FIG. 1, PD cycler 18, glucose sensor 100, medical device 120 communicate with control circuitry 30 via wireless signals 32. Control circuitry 30 and one or all of PD cycler 18, glucose sensor 100, or medical device 120 may communicate using any of a variety of local wireless communication techniques, such as radio frequency (RF) communication according to the 802.11 or Bluetooth® specification sets, infrared (IR) communication according to the IRDA specification set, or other standard or proprietary telemetry protocols, or via remote telemetry such as, for example, via a local area network (LAN), wide area network (WAN), public switched telephone network (PSTN), or cellular telephone network.

Control circuitry 30 may also communicate with another computing device via a wired or wireless connection using any of any of the local or remote wireless communication techniques discussed with respect to communication between PD cycler 18, glucose sensor 100, medical device 120 and control circuitry 30. Control circuitry 30 may also communicate with other computing devices via exchange of removable media, such as magnetic or optical disks, memory cards, or memory sticks.

Figure 2:
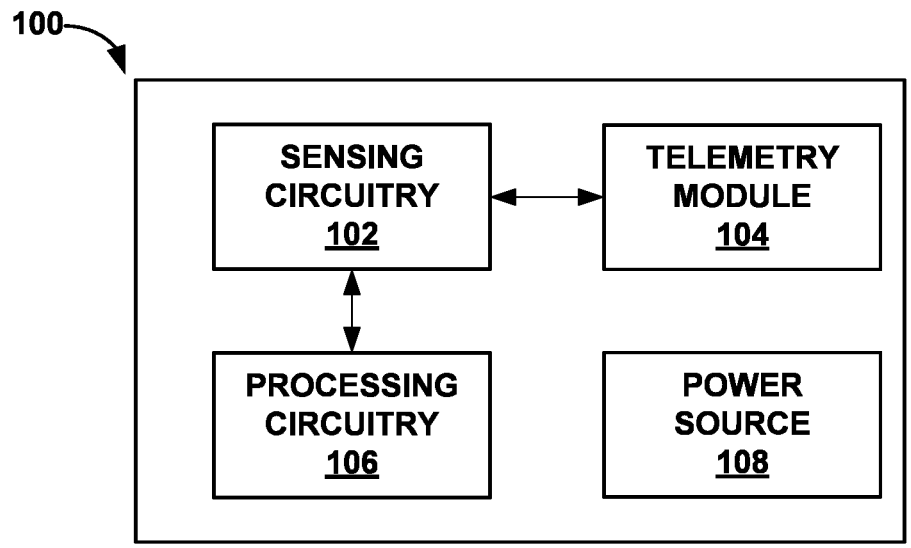
FIG. 2 is a block diagram illustrating an example blood glucose sensor configured to measure a blood glucose level of a patient.

Glucose sensor 100 can be any suitable glucose sensor configured to generate a signal indicative of a blood glucose level of patient 12. FIG. 2 is a block diagram illustrating an example glucose sensor 100 configured to measure a blood glucose level of a patient. Glucose sensor 100 includes sensing circuitry 102, telemetry module 104, processing circuitry 106, and power source 108. In some examples, glucose sensor 100 may be a continuous glucose monitor such as a Guardian™ Connect from Medtronic plc of Dublin, Ireland.

Processing circuitry 106 is configured to control sensing circuitry 102 to generate one or more signals indicative of a blood glucose level of patient 12. For example, sensing circuitry 102 can include circuitry capable of generating a signal that changes as a function of an electric current generated by an enzymatic reaction with glucose molecules in interstitial tissue of patient 12, e.g., sensing circuitry 102 may sense a blood glucose level of patient 12 subcutaneously. In some examples, sensing circuitry 102 can include circuitry capable of generating a signal that changes as a function of an electric current generated by an enzymatic reaction with glucose molecules in the blood or a blood sample of patient 12, e.g., sensing circuitry 102 may be a part of a blood glucose meter. In some examples, sensing circuitry 102 includes an electrical conductivity sensor, an electrical resistance sensor, an electrical current and/or voltage sensor, or any other suitable sensing capabilities.

In some examples, sensing circuitry 102 is configured to generate and/or transmit the signal at predetermined time intervals, which may be determined by a clinician and input to processing circuitry 106 of glucose sensor 100 via user interface 402 (FIG. 4) or input to control circuitry 30 configured to control glucose sensor 100. In other examples, sensing circuitry 102 may be configured to generate and/or transmit the signal after glucose sensor 100 receives a request from control circuitry 30.

Processing circuitry 106 may include any processing circuitry, such as, for example, any one or more of a microprocessor, a controller, a DSP, ASIC, FPGA, or equivalent discrete or integrated logic circuitry. In some examples, processing circuitry may include multiple components, such as any combination of one or more microprocessors, one or more controllers, one or more DSPs, one or more ASICs, or one or more FPGAs, as well as other discrete or integrated logic circuitry. The functions attributed to processing circuitry described herein may be embodied as firmware, hardware, software or any combination thereof. Processing circuitry controls sensing circuitry 102 to generate one or more signals indicative of a blood glucose level of patient 12.

In some examples, processing circuitry 106 is configured to send the signal from sensing circuitry 102 to control circuitry 30 (FIG. 1), e.g., via telemetry module 104. Other types of information may also be transmitted to control circuitry 30, such as the timing of the generation of the signals. In other examples, processing circuitry 106 may send the generated signal after being interrogated by control circuitry 30 to send the signals.

Telemetry module 104 includes any suitable hardware, firmware, software or any combination thereof for communicating with another device, such as control circuitry 30 (FIG. 1). Under the control of processing circuitry, telemetry module 104 may receive downlink telemetry from and send uplink telemetry to control circuitry 30 with the aid of an antenna, which may be internal and/or external. Processing circuitry 106 may provide the data to be uplinked to control circuitry 30 and the control signals for the telemetry circuit within telemetry module 104, e.g., via an address/data bus. In some examples, telemetry module 104 may provide received data to processing circuitry via a multiplexer.

The various components of glucose sensor 100 are coupled to power source 108, which may include a rechargeable or non-rechargeable battery. In some examples, a non-rechargeable battery may be selected to last for several years, while a rechargeable battery may be inductively charged from an external device, e.g., on a daily or weekly basis.

Figure 3:
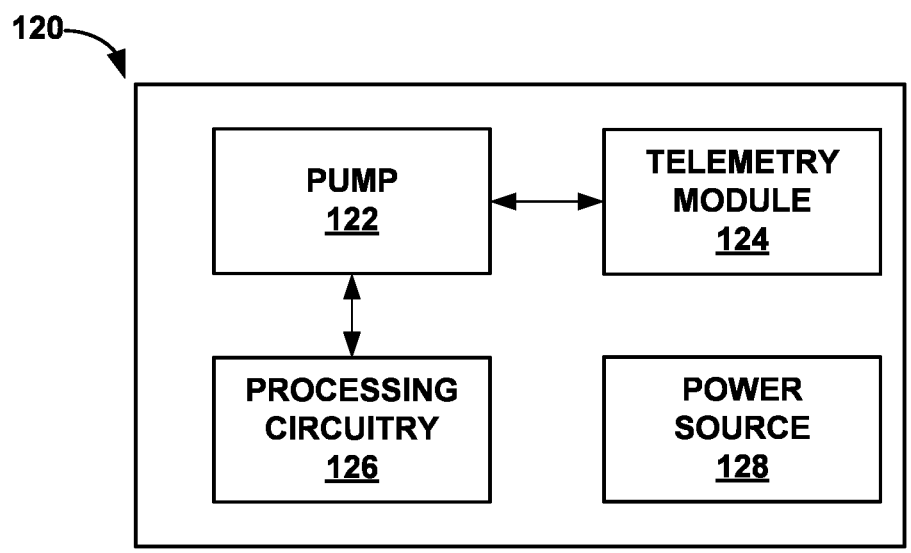
FIG. 3 is a block diagram illustrating an example insulin pump configured to deliver insulin to a patient.

Medical device 120 can be any suitable medical device configured to deliver insulin to a patient. FIG. 3 is a block diagram illustrating an example medical device 120 configured to deliver insulin. Medical device 120 includes pump 122, telemetry module 124, processing circuitry 126, and power source 128. In some examples, medical device 120 may be a continuous glucose monitor or an insulin pump such as a MiniMed™ insulin pump from Medtronic plc of Dublin, Ireland.

Processing circuitry 126 is configured to control pump 122 to cause insulin to be delivered to patient 12. For example, pump 122 is be configured to deliver a short acting or long acting insulin to be delivered through a catheter placed subcutaneously in patient 12. In some examples, pump 122 is configured to deliver a variable amount of insulin, e.g., a bolus, such as around meal times or in response to a sensed blood glucose level of patient 12. For example, telemetry module 124 of medical device 120 may receive a command from control circuitry 30 to deliver insulin to patient 12 based on a blood glucose level sensed by glucose sensor 100. Processing circuitry 126 may receive the command and cause pump 122 to deliver insulin to patient 12 continuously, e.g., at a basal rate to mimic the pancreas, and/or to deliver insulin to patient 12 at one or more particular times, e.g., a bolus, and/or to deliver insulin to patient 12 non-continuously at one or more particular times, e.g., in response to a received command. In some examples, processing circuitry 126 and/or control circuitry 30 may be configured to output an indication to a user to deliver insulin to patient 12 manually, e.g., via a syringe or an insulin pen.

Processing circuitry 126 may include any processing circuitry, such as, for example, any one or more of a microprocessor, a controller, a DSP, ASIC, FPGA, or equivalent discrete or integrated logic circuitry. In some examples, processing circuitry may include multiple components, such as any combination of one or more microprocessors, one or more controllers, one or more DSPs, one or more ASICs, or one or more FPGAs, as well as other discrete or integrated logic circuitry. The functions attributed to processing circuitry described herein may be embodied as firmware, hardware, software or any combination thereof.

In some examples, processing circuitry 126 is configured to send a signal to control circuitry 30 (FIG. 1), e.g., via telemetry module 124. For example, processing circuitry 126 may send a signal indicating whether insulin was delivered and one or more insulin delivery parameters, e.g., a type of insulin delivered, an amount of insulin delivered, an insulin delivery rate, a type and amount of insulin available to be delivered, and the like. Other types of information may also be transmitted to control circuitry 30, such as the timing of insulin delivery, e.g., one or more times at which insulin was delivered and/or one or more times at which insulin is scheduled to be delivered. In other examples, processing circuitry 126 may send the generated signal after being interrogated by control circuitry 30 to send the signals.

Telemetry module 124 includes any suitable hardware, firmware, software or any combination thereof for communicating with another device, such as control circuitry 30 (FIG. 1). Under the control of processing circuitry, telemetry module 124 may receive downlink telemetry from and send uplink telemetry to control circuitry 30 with the aid of an antenna, which may be internal and/or external. Processing circuitry 126 may provide the data to be uplinked to control circuitry 30 and the control signals for the telemetry circuit withi2 telemetry module 124, e.g., via an address/data bus. In some examples, telemetry module 104 may provide received data to processing circuitry via a multiplexer.

The various components of medical device 120 are coupled to power source 128, which may include a rechargeable or non-rechargeable battery. In some examples, a non-rechargeable battery may be selected to last for several years, while a rechargeable battery may be inductively charged from an external device, e.g., on a daily or weekly basis.

In some examples, glucose sensor 100 and medical device 120 are incorporated into a common housing. In other examples, glucose sensor 100 and medical device 120 are physically separate devices.

Figure 4:
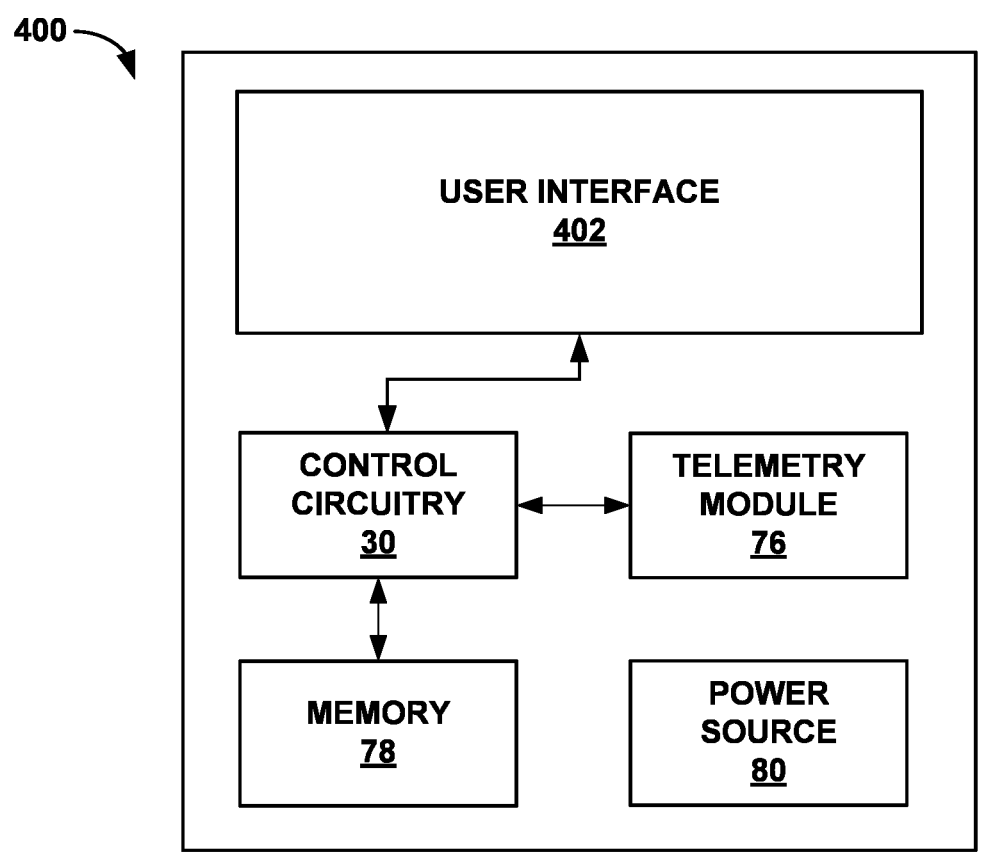
FIG. 4 is a block diagram illustrating an example computing device configured to receive a signal from a blood glucose sensor and determine information about a patient or a PD treatment of the patient based on the signal.

FIG. 4 is block diagram of an example device 400 including control circuitry 30. Device 400 further includes user interface 402, telemetry module 76, memory 78, and power source 80. Device 400 may be a dedicated hardware device with dedicated software for functioning in accordance with the disclosed techniques. Alternatively, device 400 may be an off-the-shelf computing device running an application that enables device 400 to function in accordance with the disclosed techniques.

In some examples, a user may use device 400 to obtain information about a PD treatment of a patient or control PD treatment delivered by PD cycler 18 (FIG. 1). For example, such information may be used to adjust one or more parameters of the PD treatment; diagnose and treat various conditions; observe trends relating to the PD treatment; improve the PD treatment, patient experience, and/or patient condition; or the like. The user may interact with device 400 via user interface 402, which may include display to present graphical user interface to a user, and a keypad or another mechanism for receiving input from a user.

Memory 78 may store instructions that cause control circuitry 30 to provide the functionality ascribed to control circuitry 30 and device 400 herein, and information used by control circuitry 30 to provide the functionality ascribed to control circuitry 30 and device 400 herein. For example, memory 78 may store one or more predetermined threshold values such as blood glucose level threshold values, characteristics of parameters, trends of parameters, trends of characteristics of parameters, values, and/or trends of values described herein. Additionally, or alternatively, memory 78 may store historical data or historical signals and/or trends of such historical data or signals. For example, memory 78 may store historical signals received from glucose sensor 100 such that control circuitry 30 is able to determine a trend over time in a characteristic of a parameter indicated by the signal, in accordance with the techniques of the disclosure.

Memory 78 may also store information that enables device 400 to communicate with and/or control glucose sensor 100 (or any other sensor described herein), such as, when to generate a signal indicative of a blood glucose level or to send a generated signal to device 400. Memory 78 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 78 comprises executable instructions for causing the control circuitry 30 to perform the actions attributed to it.

Device 400 may communicate wirelessly with any or all of glucose sensor 100 (FIG. 2), medical device 120 (FIG. 3), PD cycler 18 (FIG. 1), or another device, such as using RF communication, proximal inductive interaction, or other communication techniques. This wireless communication is possible through the use of telemetry module 76, which may be coupled to an internal antenna or an external antenna. Telemetry module 76 may be similar to telemetry module 104 of glucose sensor 100 and/or telemetry module 124 of medical device 120. Telemetry module 76 may also be configured to communicate with another computing device via wireless communication techniques, or direct communication through a wired connection. Examples of local wireless communication techniques that may be employed to facilitate communication between device 400 and another computing device include RF communication according to the 802.11 or Bluetooth® specification sets, infrared communication, e.g., according to the IrDA standard, or other standard or proprietary telemetry protocols. In this manner, other external devices may be capable of communicating with device 400 without needing to establish a secure wireless connection.

Power source 80 is configured to deliver operating power to the components of device 400. Power source 80 may include a battery and a power generation circuit to produce the operating power. In some embodiments, the battery may be rechargeable to allow extended operation. Recharging may be accomplished by electrically coupling power source 80 to a cradle or plug that is connected to an alternating current (AC) outlet. Additionally, or alternatively, recharging may be accomplished through proximal inductive interaction between an external charger and an inductive charging coil within device 400. In other embodiments, traditional batteries (e.g., nickel cadmium or lithium ion batteries) may be used. In addition, device 400 may be directly coupled to an alternating current outlet. In some examples, power source 80 may include circuitry to monitor power remaining within a battery. In this manner, user interface 402 may provide a current battery level indicator or low battery level indicator when the battery needs to be replaced or recharged. In some cases, power source 80 may be capable of estimating the remaining time of operation using the current battery.

The architecture of glucose sensor 100, medical device 120, and device 400 illustrated in FIGS. 2-4 is merely one example of glucose sensor 100, medical device 120, and device 400 and should not be limited to the illustrated architectures. In other examples, glucose sensor 100, medical device 120, and device 400 may be configured in a variety of other ways. For example, although processing circuitry 106 and 126 and telemetry modules 104 and 124 are described as separate modules, in some examples, processing circuitry 106 and telemetry module 104 may be functionally integrated, and processing circuitry 126 and telemetry module 124. In some examples, processing circuitry 106 and 126 and telemetry modules 104 and 124 may correspond to individual hardware units, such as ASICs, DSPs, FPGAs, or other hardware units. Further, although not shown in FIGS. 2-3, glucose sensor 100 and medical device 120 may include a memory, such as a memory like memory 78 of device 400.

As discussed above, in some examples, glucose sensor 100 and/or medical device 120 may be remotely located from control circuitry 30 (and device 400). In these examples, glucose sensor 100 and/or medical device 120 may transmit sensed signals or other data generated based on the signals to control circuitry 30 via any suitable communication.

During operation, glucose sensor 100 and/or medical device 120 may generate one or more signals indicative of one or more parameters of PD treatment or patient 12. Glucose sensor 100 and/or medical device 120 may send the respective signal to control circuitry 30 either wirelessly or wired connection for processing and analysis. For example, glucose sensor 100 may send control circuitry 30 a signal indicative of a blood glucose level of patient 12, or medical device 120 may send a signal indicative of a confirmation of delivery of insulin to patient 12. Control circuitry 30 may compare a characteristic, such as an amplitude, of the signal to a predetermined threshold value, determine a trend in the characteristic of the signal, or both. Additionally, or alternatively, control circuitry 30 may determine a value (e.g., a blood glucose level) based on the signal. Then, control circuitry 30 may take one or more actions (e.g., control PD cycler 18, medical device 120, glucose sensor 100, and/or generate alerts) after analyzing the data, such as by comparing the characteristic to a predetermined threshold value, determining a trend in the characteristic, determining a value, or combinations thereof. In all examples described herein, communication of a signal may refer to the raw signal generate by glucose sensor 100 and/or medical device 120 or other data generated based on the raw signal.

As discussed above, in some examples, control circuitry 30 is configured to determine one or more parameters related to PD treatment delivered by PD system 10 based on signals generated by glucose sensor 100, medical device 120, and/or PD cycler 18. A parameter related to PD treatment can include, for example, an amount, rate, time, and type of insulin for delivery of insulin by medical device 120, a blood glucose level of patient 12 sensed by glucose sensor 100, a blood glucose threshold level, an ultrafiltration goal of patient 12, a transport characteristic of patient 12, a PD dialysate glucose concentration, a PD dialysate alternate osmotic solute and its concentration, an ultrafiltration and/or PD dialysate volume, a PD dialysate dwell time, and/or any other suitable PD treatment parameter.

Figure 5:
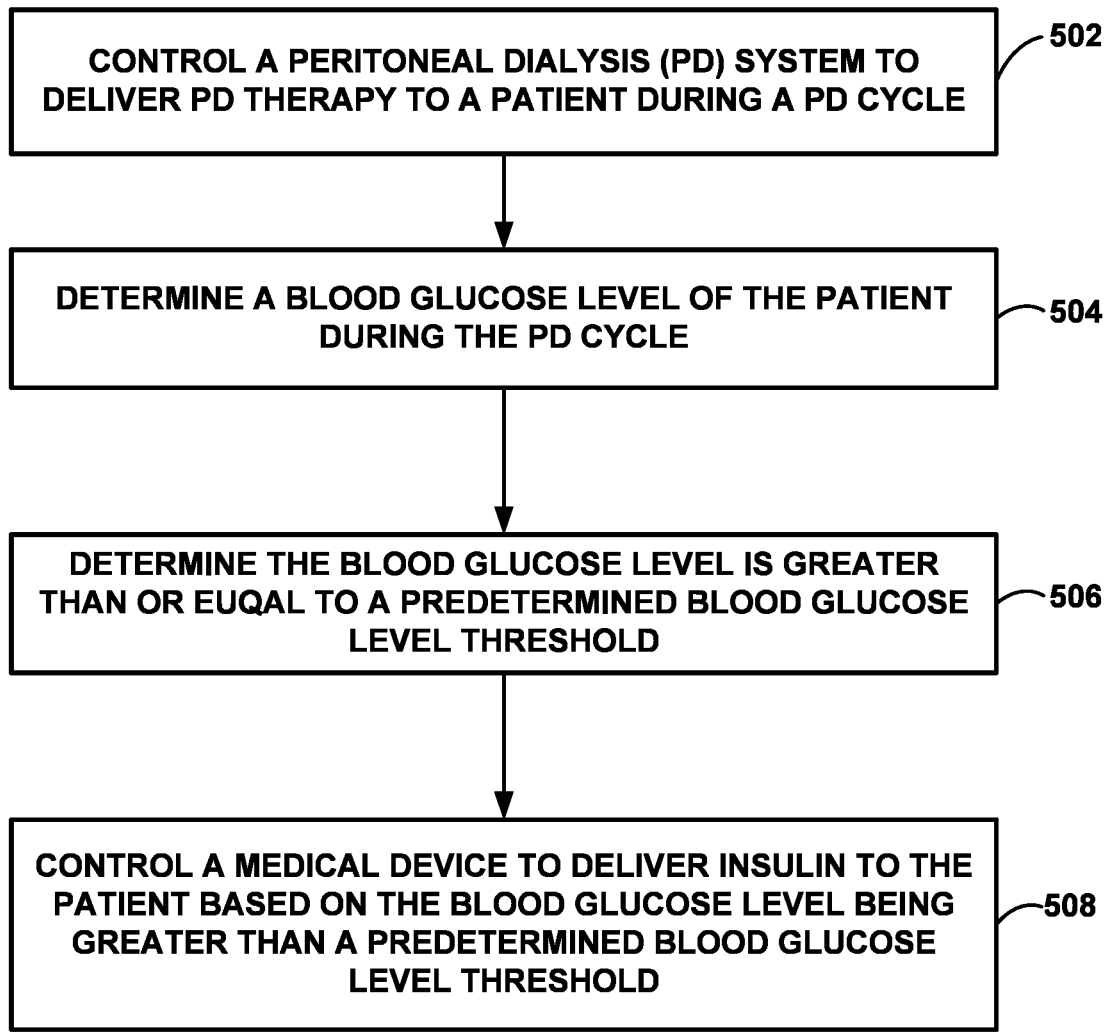
FIG. 5 is a flow diagram of an example technique for providing PD treatment with glycemic control based on a signal generated by a blood glucose sensor.

FIG. 5 is a flow diagram of an example technique for providing PD treatment with glycemic control based on a signal generated by a blood glucose sensor. The example technique of FIG. 5 is described with respect to PD system 10 of FIG. 1. In other examples, however, the example technique of FIG. 5 may be performed by a PD system including another glucose sensor 100, medical device 120, or PD cycler 18. In addition, although control circuitry 30 is primarily referred to throughout the description of FIG. 5, in other examples, the techniques described may be performed by processing circuitry of another device, alone or in combination with control circuitry 30.

Control circuitry 30 controls a PD system to deliver PD therapy to a patient (502). For example, control circuitry 30 may generate and send a command message, via telemetry module 76, to cause PD cycler 18 to deliver a dialysate into peritoneal cavity 16 via catheter 14 and to cause PD cycler 18 to remove fluid from peritoneal cavity 16 via catheter 14 after a dwell time, e.g., to deliver a PD cycle to patient 12.

In some examples, control circuitry 30 may control PD system 10 to deliver PD therapy to patient 12 over a period of time, e.g., an hour, a day, a week, a month, or many months, e.g., by delivering a plurality of PD cycles to patient 12 periodically, according to a schedule, and/or in response to a determination that patient 12 should receive PD therapy corresponding to a respective PD cycle. For example, control circuitry 30 may cause PD cycler 18 to deliver a first PD cycle to patient 12, wait for a period of time, and deliver a second PD cycle to patient 12. In some examples, a PD cycle may include delivery of a PD dialysate to peritoneal cavity 16 of patient 12, e.g., via PD cycler 18, a dwell time in which the PD dialysate draws fluid and waste material through the peritoneum of patient 12 via osmosis, and removal of the fluid from peritoneal cavity 16 of patient 12, e.g., via PD cycler 18. PD therapy and/or treatment may comprise delivering one or more PD cycles to patient 12, e.g., periodically, according to a schedule, or in response to a determination that a PD cycle should be delivered to the patient.

Control circuitry 30 determines a blood glucose level of the patient during a PD cycle (504). For example, control circuitry 30 may receive a signal indicative of the blood glucose level from glucose sensor 100 during a PD cycle, and may determine a blood glucose level of patient 12 based on the received signal. In some examples, glucose sensor 100 may sense a blood glucose level of patient 12 subcutaneously, e.g., glucose sensor 100 may be a CGM and may sense the glucose level of patient 12 periodically, according to a schedule, or in response to a command received (via telemetry module 104) from control circuitry 30 to sense the blood glucose level of patient 12.

In some examples, control circuitry 30 may determine a blood glucose level of patient 12 before or after a PD cycle. For example, control circuitry 30 may determine a blood glucose level of patient 12 before PD cycler 18 delivers a PD cycle to patient 12, and/or control circuitry 30 may determine a blood glucose level of patient 12 after PD cycler 18 delivers a PD cycle. In other words, (502) and (504) may occur in reverse order, e.g., control circuitry 30 may control PD system 10 to deliver PD therapy to patient 12 at (502) after control circuitry 30 determines a blood glucose level of patient 12 at (504).

Control circuitry 30 determines the blood glucose level indicated by the received sensor signal is greater than or equal to the predetermined blood glucose level threshold (506). For example, the predetermined blood glucose level threshold may be stored in memory 78 of device 400 (FIG. 4) or a memory of another device.

Control circuitry 30 controls a medical device to deliver insulin to the patient based on the blood glucose level being greater than or equal to a predetermined blood glucose level threshold (508). In response to determining the blood glucose level indicated by the received sensor signal is greater than or equal to the predetermined blood glucose level threshold, control circuitry 30 generates and sends, via telemetry module 76, a command signal to medical device 120 to deliver insulin to patient 12. In some examples, in response to receiving such a command, medical device 120 may deliver insulin to patient 12 subcutaneously. For example, medical device 120 may be an insulin pump configured to deliver insulin to patient 12 subcutaneously.

In some examples, control circuitry 30 may control PD cycler 18 to cease delivering the PD therapy to patient 12 in response to determining that the blood glucose level is greater than or equal to the predetermined blood glucose level threshold. For example, control circuitry 30 may generate and send a command signal to PD cycler 18 to cut the dwell time of a PD cycle short and remove fluid, including the PD dialysate, from peritoneal cavity 16 of patient 12.

In some examples, control circuitry 30 may determine a second blood glucose level of patient 12 at a second time after the time at which the blood glucose level of patient 12 was determined in block 504. In other words, the determined blood glucose level at block 504 may be a first blood glucose level of patient 12 at a first time, and control circuitry 30 may determine a second blood glucose level of patient 12 at a second time after the first time, e.g., after having controlled PD cycler 18 to cease delivery of PD to patient 12 by removing the fluid thereby decreasing or ceasing absorption of glucose from the PD dialysate by patient 12 by the removal of the PD dialysate. Control circuitry 30 may then control PD cycler 18 to resume delivery of the PD therapy to patient 12 in response to determining that the second blood glucose level is less than the predetermined blood glucose level threshold. For example, a period of time may have passed since ceasing PD therapy in which the blood glucose level of patient 12 may decrease naturally or via insulin delivered to patient 12, e.g., by medical device 120. If an ultrafiltration goal of patient 12 was not met because of ceasing the PD cycle, control circuitry 30 may cause PD cycler 18 to resume the PD cycle and/or initiate a new PD cycle after the blood glucose level of patient 12 is less than the threshold.

In some examples, control circuitry 30 may further determine PD therapy parameters based on the glucose level of patient 12. For example, control circuitry 30 may determine a PD dialysate glucose concentration (e.g., 1.25% dextrose, 2.5% dextrose, 4.25% dextrose, and the like) based on a PD dialysis ultrafiltration goal and the glucose level of patient 12. Control circuitry 30 may further determine an ultrafiltration volume, e.g., a PD dialysate volume, and a PD dialysate dwell time based on a transport characteristic of patient 12, the determined PD dialysate glucose concentration, and the blood glucose level of patient 12. Control circuitry 30 may then control PD cycler 18 to deliver PD therapy, e.g., one or more PD cycles, to patient 12 in accordance with the determined ultrafiltration volume, the determined PD dialysate glucose concentration and dwell time.

In some examples, control circuitry 30 may further change PD therapy parameters over the course of delivery of PD therapy, e.g., via one or more PD cycles. For example, control circuitry 30 may cause PD system 10 to deliver PD therapy to patient 12 that decreases the glucose concentration of the PD dialysate over time based on how well the glucose level of patient 12 is under control. In some examples, after determining, at a first time, a first set of one or more PD therapy parameters such as a first PD dialysate glucose concentration, volume and dwell time based on a first determined glucose level, ultrafiltration goal, and transport characteristic of patient 12, control circuitry 30 may determine a second set of PD therapy parameters at a second time. For example, control circuitry 30 may determine a second blood glucose level of patient 12 at a second time after delivery of PD to the patient, and control circuitry 30 may determine a second PD dialysate glucose concentration based on the second glucose level of the patient. Control circuitry 30 may determine a second ultrafiltration volume and PD dialysate dwell time based on the transport characteristic and determined second PD dialysate glucose concentration and blood glucose level. Control circuitry 30 may control PD cycler 18 to deliver the PD therapy to the patient in accordance with the determined second ultrafiltration volume, the determined second PD dialysate glucose concentration, and the determined second PD dialysate dwell time. In some examples, the second PD dialysate glucose concentration may be less than the first PD dialysate glucose concentration. In some examples, the second PD dialysate dwell time may be less than the first PD dialysate dwell time.

As described above, the use of shorter, frequent dialysis exchanges may increase the net ultrafiltration volume relative to the amount of glucose absorbed by the patient. In some examples, control circuitry 30 may determine the second set of PD therapy parameters and a time between delivery of PD cycles such that PD is delivered to patient 12 via shorter, more frequent PD dialysis exchanges and/or cycles.

In some examples, control circuitry 30 may determine other PD therapy parameters as well, such as the type of PD dialysate solute. Control circuitry 30 may determine a PD dialysate comprising an alternate osmotic solute and a PD dialysate concentration of the alternate osmotic solute. For example, alternate PD dialysate osmotic solutes such as a glucose polymer may be absorbed at a lower rate or to a lesser extent than dextrose. In some examples, alternate osmotic solutes such as amino acids may reduce and/or eliminate glucose from the PD dialysate to be absorbed. In examples where it is difficult to achieve an ultrafiltration goal while still maintaining glycemic control because of absorption of glucose by patient 12, e.g., even with closed loop control of PD therapy and the delivery of insulin, control circuitry 30 may determine to switch out the PD dialysis solute type in order to achieve the ultrafiltration goal while still maintaining glycemic control.

For example, based on the glucose level of patient 12, control circuitry 30 may determine a PD dialysate including an alternate osmotic solute and its concentration, and control circuitry 30 may determine an ultrafiltration or PD dialysate volume and dwell time based on the blood glucose level, transport characteristic, and PD dialysate alternate osmotic solute and its concentration. Control circuitry 30 may then control PD cycler 18 to deliver PD therapy to patient 12 in accordance with the determined ultrafiltration volume, PD dialysate alternate osmotic solute concentration, and dwell time.

In some examples, PD system 10 and control circuitry 30 may provide PD therapy to patient 12 while maintaining glycemic control of the blood glucose level of patient 12 in a continuous and/or closed loop manner. For example, control circuitry 30 may determine the blood glucose level of patient 12 a predetermined intervals during delivery of PD therapy to patient 12, e.g., before, after, or during one or more PD cycles. Control circuitry 30 may control medical device 120 to deliver insulin to patient 12 at predetermined intervals, e.g., while the most recent determined blood glucose level is greater than or equal to the blood glucose level threshold.

The techniques described in this disclosure, including those attributed to glucose sensor 100, medical device 120, PD cycler 18, control circuitry 30, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
controlling, by control circuitry, a peritoneal dialysis (PD) device to deliver PD therapy to a patient during a current PD cycle;
determining, by the control circuitry, a blood glucose level of the patient during the current PD cycle;
determining, by the control circuitry, the blood glucose level is greater than or equal to a predetermined blood glucose level threshold during the current PD cycle;
controlling, by the control circuitry and in response to determining the blood glucose level is greater than or equal to the predetermined blood glucose level threshold, a medical device to deliver insulin to the patient during the current PD cycle; and
in response to the medical device delivering insulin to the patient during the current PD cycle, determining, by the control circuitry a modification to a parameter of the PD therapy during the current PD cycle, wherein the parameter comprises at least one of a dialysate glucose concentration, an alternate osmotic solute concentration, a PD dialysate volume, a PD dialysate dwell time, an ultrafiltration volume, or a number of PD cycles within a time period.

2. The method of claim 1, wherein determining the blood glucose level comprises receiving, by the control circuitry, a signal indicative of the blood glucose level from a glucose sensor.

3. The method of claim 2, further comprising:
sensing, by the glucose sensor, the blood glucose level of the patient subcutaneously.

4. The method of claim 1, further comprising:
controlling, by the control circuitry, the PD device to cease delivering the PD therapy to the patient in response to determining that the blood glucose level is greater than or equal to the predetermined blood glucose level threshold.

5. The method of claim 4, wherein the blood glucose level of the patient comprises a first blood glucose level at a first time, the method further comprising:
determining, by the control circuitry, a second blood glucose level of the patient at a second time; and
controlling the PD device to resume delivery of the PD therapy to the patient in response to determining that the second blood glucose level is less than the predetermined blood glucose level threshold.

6. The method of claim 1, further comprising:
determining, by the control circuitry and based on the blood glucose level of the patient and a PD dialysis ultrafiltration goal, the dialysate glucose concentration;
determining, by the control circuitry and based on a transport characteristic of the patient, the dialysate glucose concentration, the blood glucose level of the patient, and the PD dialysis ultrafiltration goal, an ultrafiltration volume for the patient and the PD dialysate dwell time; and
controlling, by the control circuitry, the PD device to deliver the PD therapy to the patient in accordance with the ultrafiltration volume, the dialysate glucose concentration, and the PD dialysate dwell time.

7. The method of claim 6, wherein the blood glucose level of the patient comprises a first blood glucose level at a first time, wherein the dialysate glucose concentration is a first dialysate glucose concentration, wherein the ultrafiltration volume is a first ultrafiltration volume, wherein the PD dialysate dwell time is a first PD dialysate dwell time, the method further comprising:

determining, by the control circuitry, a second blood glucose level of the patient at a second time after delivery of PD to the patient;

determining, by the control circuitry and based on the second blood glucose level of the patient, a second dialysate glucose concentration;

determining, based on the transport characteristic of the patient and the second dialysate glucose concentration and the second blood glucose level of the patient, a second ultrafiltration volume for the patient and a second PD dialysate dwell time; and controlling, by the control circuitry, the PD device to deliver the PD therapy to the patient in accordance with the second ultrafiltration volume, the second dialysate glucose concentration, and the second PD dialysate dwell time.

8. The method of claim 1, further comprising:

determining, by the control circuitry and based on the blood glucose level of the patient, a PD dialysate comprising an alternate osmotic solute and a PD dialysate alternate osmotic solute concentration of the alternate osmotic solute;

determining, by the control circuitry and based on a transport characteristic of the patient and the PD dialysate alternate osmotic solute concentration and the blood glucose level of the patient, the ultrafiltration volume and the PD dialysate dwell time; and controlling, by the control circuitry, the PD device to deliver the PD therapy to the patient in accordance with the ultrafiltration volume, the PD dialysate alternate osmotic solute concentration, and the PD dialysate dwell time.

9. The method of claim 8, wherein the alternate osmotic solute comprises at least one of a glucose polymer or an amino acid.

10. The method of claim 1, further comprising delivering, by the medical device, insulin to the patient subcutaneously.

11. The method of claim 1, wherein determining the blood glucose level of the patient comprises determining the blood glucose level of the patient at first predetermined intervals during delivery of PD therapy to the patient, wherein controlling the medical device to deliver insulin to the patient comprises controlling the medical device to deliver insulin to the patient at second predetermined intervals and while the most recent determined blood glucose level determined at the first predetermined intervals is greater than or equal to the blood glucose level threshold.

12. A system comprising:

a glucose sensor configured to generate a signal indicative of a blood glucose level of a patient;

a medical device configured to deliver insulin to the patient;

a peritoneal dialysis (PD) device; and control circuitry configured to:

control the PD device to deliver PD therapy to a patient during a current PD cycle, determine, based on the signal, the blood glucose level of the patient during the current PD cycle, determine that the blood glucose level is greater than or equal to a predetermined blood glucose level threshold during the current PD cycle, control, in response to determining the blood glucose level is greater than or equal to the predetermined blood glucose level threshold, the medical device to deliver insulin to the patient during the current PD cycle; and in response to the medical device delivering insulin to the patient during the current PD cycle, determine a modification to a parameter of the PD therapy during the current PD cycle, wherein the parameter comprises at least one of a dialysate glucose concentration, an alternate osmotic solute concentration, a PD dialysate volume, a PD dialysate dwell time, an ultrafiltration volume, or a number of PD cycles within a time period.

13. The system of claim 12, wherein the glucose sensor is configured to sense the blood glucose level of the patient subcutaneously, wherein the medical device is configured to deliver insulin to the patient subcutaneously.

14. The system of claim 12, wherein the blood glucose level is a first blood glucose level determined at a first time, wherein the control circuitry is further configured to:

control the PD device to cease delivering the PD therapy to the patient in response to determining that the first blood glucose level is greater than the predetermined blood glucose level threshold;

determine a second blood glucose level of the patient at a second time; and control the PD device to resume delivery of the PD therapy to the patient in response to determining that the second blood glucose level is less than the predetermined blood glucose level threshold.

15. The system of claim 12, wherein the control circuitry is further configured to:

determine, based on the blood glucose level of the patient and a PD dialysis ultrafiltration goal, the dialysate glucose concentration;

determine, based on a transport characteristic of the patient, the dialysate glucose concentration, the blood glucose level of the patient, and the PD dialysis ultrafiltration goal, an ultrafiltration volume for the patient and the PD dialysate dwell time; and control the PD device to deliver the PD therapy to the patient in accordance with the ultrafiltration volume, the dialysate glucose concentration, and the PD dialysate dwell time.

16. The system of claim 15, wherein the blood glucose level of the patient comprises a first blood glucose level at a first time, wherein the dialysate glucose concentration is a first dialysate glucose concentration, wherein the ultrafiltration volume is a first ultrafiltration volume, wherein the PD dialysate dwell time is a first PD dialysate dwell time, wherein the control circuitry is further configured to:

determine a second blood glucose level of the patient at a second time after delivery of PD to the patient;

determine based on the second blood glucose level of the patient, a second dialysate glucose concentration;

determine, based on the transport characteristic of the patient and the second dialysate glucose concentration and the second blood glucose level of the patient, a second ultrafiltration volume for the patient and a second PD dialysate dwell time; and control the PD device to deliver the PD therapy to the patient in accordance with the second ultrafiltration volume, the second dialysate glucose concentration, and the second PD dialysate dwell time.

17. The system of claim 12, wherein the control circuitry is further configured to:

determine, based on the blood glucose level of the patient, a PD dialysate comprising an alternate osmotic solute and a PD dialysate alternate osmotic solute concentration of the alternate osmotic solute;

determine, based on a transport characteristic of the patient and the PD dialysate alternate osmotic solute concentration and the blood glucose level of the patient, the ultrafiltration volume and the PD dialysate dwell time; and control the PD device to deliver the PD therapy to the patient in accordance with the ultrafiltration volume, the PD dialysate alternate osmotic solute concentration, and the PD dialysate dwell time.

18. The system of claim 17, wherein the alternate osmotic solute comprises at least one of a glucose polymer or an amino acid.

19. The system of claim 12, wherein the control circuitry is further configured to:

determine the blood glucose level of the patient at first predetermined intervals during delivery of PD to the patient; and control the medical device to deliver insulin to the patient at second predetermined intervals while the most recent determined blood glucose level determined at the first predetermined intervals is greater than or equal to the blood glucose level threshold.

* * * * *